US005952318A

United States Patent [19]
Bouic

[11] Patent Number: 5,952,318
[45] Date of Patent: Sep. 14, 1999

[54] TREATMENT OF HIV POSITIVE PATIENTS

[75] Inventor: Patrick Jacques Desire Bouic, Capetown, South Africa

[73] Assignee: Rooperol (NA) NV, Amsterdam, Netherlands

[21] Appl. No.: 09/024,299

[22] Filed: Feb. 17, 1998

[30] Foreign Application Priority Data

Feb. 18, 1997 [ZA] South Africa .................. 97/1346

[51] Int. Cl.$^6$ ............................................. A61K 31/56
[52] U.S. Cl. ........................... 514/170; 514/26; 514/934
[58] Field of Search ........................ 514/170, 26, 934

[56] References Cited

PUBLICATIONS

Xue et al., (AN 93250366, abstract of Chung–Kuo Chung Hsi I Chieh, (1992, Nov.), 12 (11) 652–5.

*Primary Examiner*—Jose' G. Dees
*Assistant Examiner*—Sabiha N. Qazi
*Attorney, Agent, or Firm*—Young & Thompson

[57] ABSTRACT

A mixture of betasitosterol and betasitosteryl glycoside in a ratio of between 1:1 and 500:1 is administered to an HIV infected individual. This has the effect of stabilizing CD4 cell numbers, decreasing the plasma viral load, degree of apoptosis in, and the serum levels of 1L6 in the peripheral blood.

5 Claims, 10 Drawing Sheets

TREATMENT OF HIV POSITIVE PATIENTS

FIELD OF THE INVENTION

Use of β-Sitosterol (BSS) and β-Sitosterol glucoside (BSSG) mixture for maitaining the immune status quo/ deferring the clinical deterioration of individulas infected with the Human Immunodeficiency Virus (HIV) or cats infected with the Feline Immunodeficiency Virus (FIV) as well as restoring the fertility potential of such compromised animals and ensuring the health of their offspring.

BACKGROUND TO THE INVENTION

The Human Immunodeficiency Virus (HIV) infects cells of the immune system, especially those bearing the CD4 membrane receptor (largely T-helper cells and a certain percentage of circulating monocytes) [1]. With time, individuals exhibit a degree of immunosuppression due to the constant loss of their CD4 cells but also largely due to the functional dysregulation of these cells (proliferation in response to antigens, cytotoxic acitivity and secretion of immunoregulatory cytokines) [2,3]. It has also been shown that disease progression is paralleled by overt autoimmune processes (thrombocytopaenia, lymphopaenia, arthritis, etc.) [4]. The loss of immune cells has been partly attributed to the increased frequency of apoptosis (programmed cell death) which is evident in the peripheral blood of HIV infected individuals [5,6]. Also of note is the fact that several reports have shown increased levels of the pro-inflammatory cytokines IL6 and TNF-α in the sera of infected persons [7,8] and it had been shown that these cytokines are capable of activating viral replication in latently infected cells.

The Feline Immunodeficiency Virus (FIV), the feline counterpart of HIV, infects immune cells of cats and induces an equivalent pathology to that induced by the HIV [9]. Indeed, the cats thus infected demonstrate immunosuppression with time (due to quantitative and qualitative CD4 cell loss and dysregulation) and finally succumb to death due to opportunistic infections. An interesting phenomenon described, is the secondary infertility associated with FIV infection. Many authors have argued that due to the similarities between HIV and FIV pathologies, the feline virus can be used as a model to study the outcome of therapies before these are attempted in human subjects.

The Applicant has previously shown (U.S. Pat. No. 5,486, 510; EPO Patent Application 92302556.3) that BSS and BSSG either on their own or preferably in a mixtrue (ratio of BSS to BSSG between 1:1 and 500:1) are capable of modulating the immune response of T cells as well as NK cells in vitro and in vivo. Indeed, the Applicant has shown that T cells are capable of increasing their proliferative responses to mitogens and enhancing their secretion of lymphokines such as IL2 and Gamma Interferon when in the presence of the BSS:BSSG mixture. In parallel, NK cells exhibit enhanced lytic activity against cancer cells when co-cultured with the BSS:BSSG mixture [10].

No claim was made in U.S. Pat. No. 5,486,510 or EPO 92302556 for the treatment of HIV positive patients because the increased T cell proliferation observed on treatment with a BSS:BSSG mixture suggested a favorable environment for HIV replication since T cells and monocytes (under the influence of monokines such as IL6 and TNFα) are used by the HIV for its replicative cycles. Treatment of HIV infections and the accompanying AIDS symptoms were therefore specifically excluded from any claims made in U.S. Pat. No. 5,486,510 and its equivalent patent applications. Nevertheless, in vitro and in vivo investigations were continued to investigate the validity of this assumption. Surprising and unexpected results obtained to date have now indicated an exciting possibility of the stabilization of CD4 cell numbers (a special T cell type preferentially infected by the HIV or FIV in humans or cats respectively) over an extended time period on treatment with BSS and BSSG mixtures with concomitant decrease in viral load, a decrease in apoptotic lymphocytes in the circulation of HIV positive patients and a significant decrease in the levels of the pro-inflammatory monokine responsible for HIV replication, namely IL6.

In this specification, the term HIV will be used to include the term FIV as well, unless otherwise specifically distinguished.

THE INVENTION

According to the invention, a method of stabilizing CD4 cell numbers in HIV infected individuals includes the administration of a mixture of BSS and BSSG, preferably in capsule form.

The ratio of BSS:BSSG may vary between 1:1 to 500:1 but it is preferred to use a ratio of the order of 100:1.

Similarly, according to the invention, a method of decreasing the plasma viral load and decreasing the degree of apoptosis of lymphocytes in the peripheral blood of mV positive patients includes the administration of the same BSS:BSSG mixture.

Also, according to the invention, a method of decreasing the serum levels of IL6 in the peripheral bloods of patients includes the administration of the same BSS:BSSG mixture.

Figure 1:
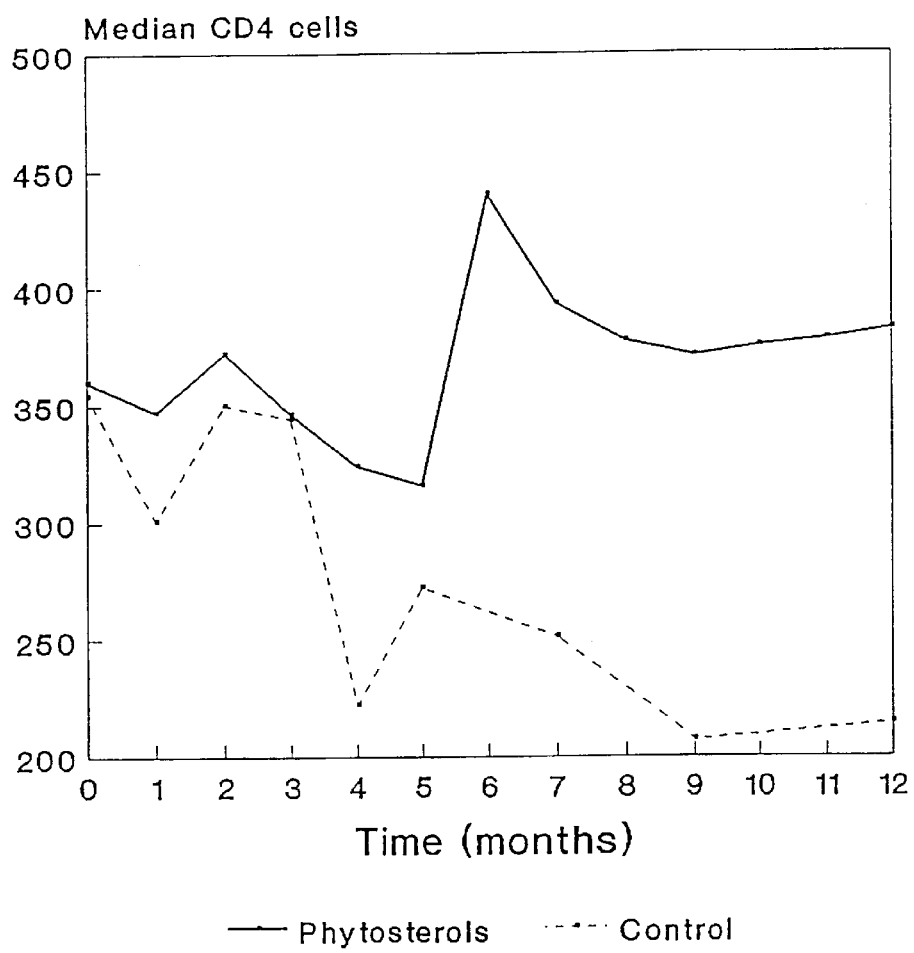
FIG. 1 shows the stability of the median CD4 cell numbers over a 12 month period.

EXPERIMENTAL PROCEDURES (1) FIV Model:

This part of the experimental procedures consists of 2 separate pilot studies: pilot study number 1 consists of 5 cats naturally infected with the FIV (unknown strain) and divided into 2 groups: one group of 3 cats received the BSS:BSSG capsules (100:1 ratio; 20mg:0.2 mg) whereas the second group of 2 cats was simply followed up but no treatment was instituted. Clinical, immunological and haematological parameters measured are given in detail below.

Pilot study number 2 consists of 33 cats all experimnetally infected with the Petaluma strain of FIV and divided into 2 groups: group 1 cats (n=16) were treated with the BSS:B-SSG capsules (per os, one capsule per day from Monday to Friday; 100:1 ratio, 20mg:0.2mg) and group 2 cats (n=17) received placebo capsules containing talcum. These cats were purpose bred, randomly selected for the study and they were obtained from a breeding colony of random source cats housed in a free access facility at the University of Stellenbosch. Male cats were neutered before the start of the study. The cats were housed in the same room at this facility in two separate walk-in cages and were fed a standard diet of commercial cat food and ad lib fresh tap water and dry cat food.

All the cats were tested for the presence of FIV antibodies using the Combo$^R$ kit. Infection of the cats was conducted using 1 ml of blood from a donor cat known to be infected with the Petaluma strain of FIV. The cats were observed daily for signs of disease or abnormal behaviour. Clinical parameters, as well as haematological- and immunological parameters were monitored and recorded weekly for the first 6 weeks and thereafter, once every 6 weeks. The parameters measured included: full blood counts; CD3, CD4 and CD8 cells in % and absolute numbers; temperature; mass; clinical signs of disease of the conjunctiva, ears, gingiva, upper and lower respiratory tract; size of four groups of lymph nodes and general condition, The pilot study number 1 lasted for 175 weeks while the study number 2 lasted 125 weeks.

(2) HIV Study:

Eighty patients infected with the HIV agreed to participate in this study. None of the patients were on concomitant anti-retroviral medication (or combinations thereof) at the time of entry into the study or during the study period. The patients were advised to ingest 2 capsules containing the BSS:BSSG 3 times per day (100:1 ratio; 20mg:0.2mg). They also gave a detailed account of any new dietary supplement which was introduced during the study period. Complete records are available for a 27 months period. The patients were seen monthly for the first 6 months and thereafter, at 3 monthly intervals. At each visit, the individuals were evaluated clinically for any signs of HIV related disease; blood was drawn for a full blood count and CD3, CD4 and CD8 cell determinations by flow cytometry using dual colour monoclonal reagents.

A sample of clotted blood was stored at −20° C. for the determination of plasma viral load by quantitative NASBA technique using commercial kits (Abbott). The results were expressed as the number of viral copies per ml of plasma.

A second sample of clotted blood was stored for the determination of serum IL6 levels using an in-house ELISA method standardized with external standards. The results were expressed as U/ml serum.

Lymphocyte apoptosis levels in the peripheral blood of patients was measured using a commercial kit (Ylem ApoTest) and flow cytometry. The results were expressed as % lymphocyte having apoptosis in the lymphocyte gate (set on SSC versus FL3 gate). The data was analyzed by calculating the median % apoptosis at baseline and again at 6 months after the initiation of therapy. Statistical significance was determined using the non-parametric Wilcoxon Rank test.

In parallel, a group of "control" patients (n=27) who were not ingesting the BSS:BSSG capsules and who were also HIV positive were followed medically at the clinic. These patients opted not to participate on the study but their immune cells (CD4 cells) were also determined using the identical procedure as for the study patients. Since these patients were not on any forms of therapy, they were followed as control patients in order to determine if the loss of their immune cells followed the known natural history of HIV infection. This group was followed over a period of 18 months.

(3) Evaluation of data:

a) FIV model:

The data generated by the FIV study number 2 was evaluated by Analysis of Variance between groups. The baseline data was analyzed in order to rule out significant differences between groups at the beginning of the study. Hence, any significant changes or differences occurring over time could only be attributed to the BSS:BSSG content of the capsules which the one group received.

b) HIV study:

The evaluation of the data obtained for the group of patients who have been on the clinical trial was analyzed by determining the median CD4 cell numbers for the group irrespective of the baseline CD4 cell number of individuals (ie. no stratification of the data was applied). The median CD4 cell number at each time point was plotted and a regression line was statistically determined.

The change in the degree of apoptosis detected in the peripheral blood of infected individuals was analyzed as the median degree of apoptosis at baseline and again at 6 months post the initiation of therapy. Similarly, the change in the serum levels of IL6 was calculated at baseline (entry into the study) and again at 6 months. Statistical significance was determined using the Wilcoxon Rank test (non-parametric method). The data is presented graphically.

As for the changes in the plasma viral loads, the data was normalized by determining the change over time as a log change (ie. value at time X divided by value at baseline expressed as a log value). The mean changes for the group was subsequently determined and plotted graphically.

RESULTS

Results of HIV Study

Figure 2:
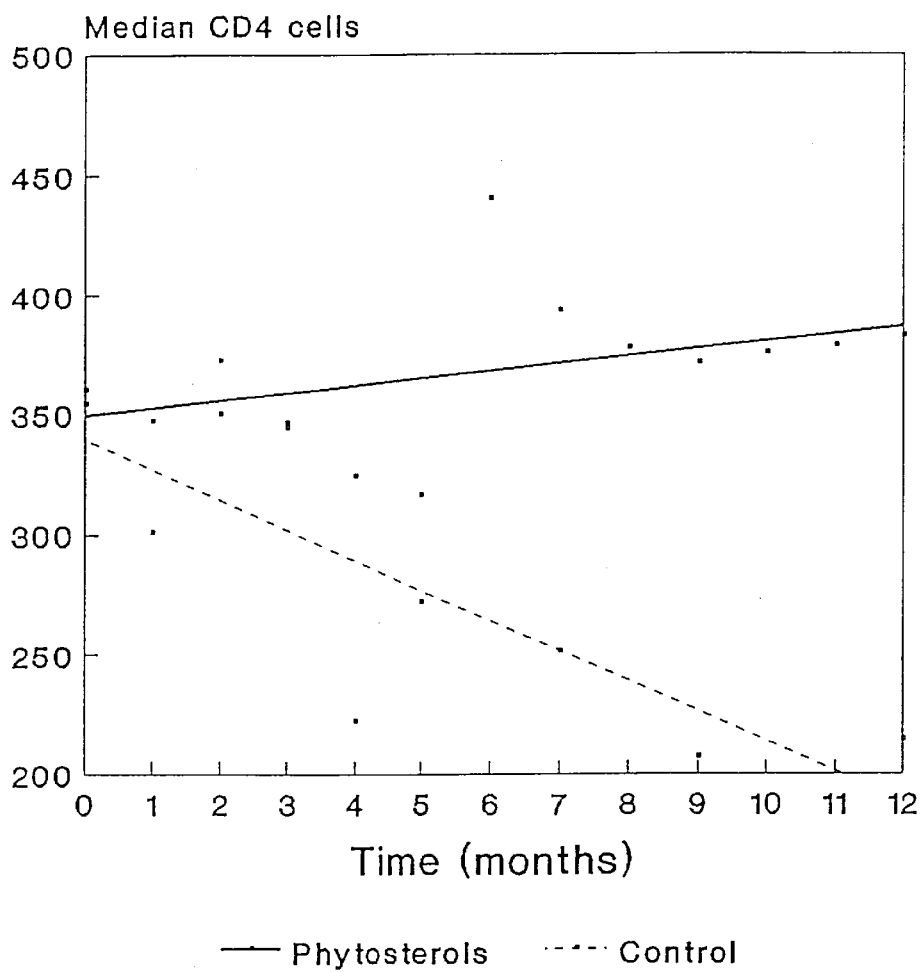
FIG. 2 shows the decline of a control group over the same 12 month period of FIG. 4.

As shown in FIG. 1, the median CD4 cell numbers exhibits stability over a period of 12 months with a slight increase in the median value relative to the baseline. This increase is not statistically significant. When represented as regression lines (same data), again the patient group (n=80) shows a stable trend whereas the control group shows the typical decline over the same time period (FIG. 2). It is published that an untreated HIV positive patient loses approximately 100–150 CD4 cells per year. Our data generated using the group of 27 patients serving as controls shows that the decline is about 150 of these cells over the 12 months period therefore confirming previous data.

Figure 3:
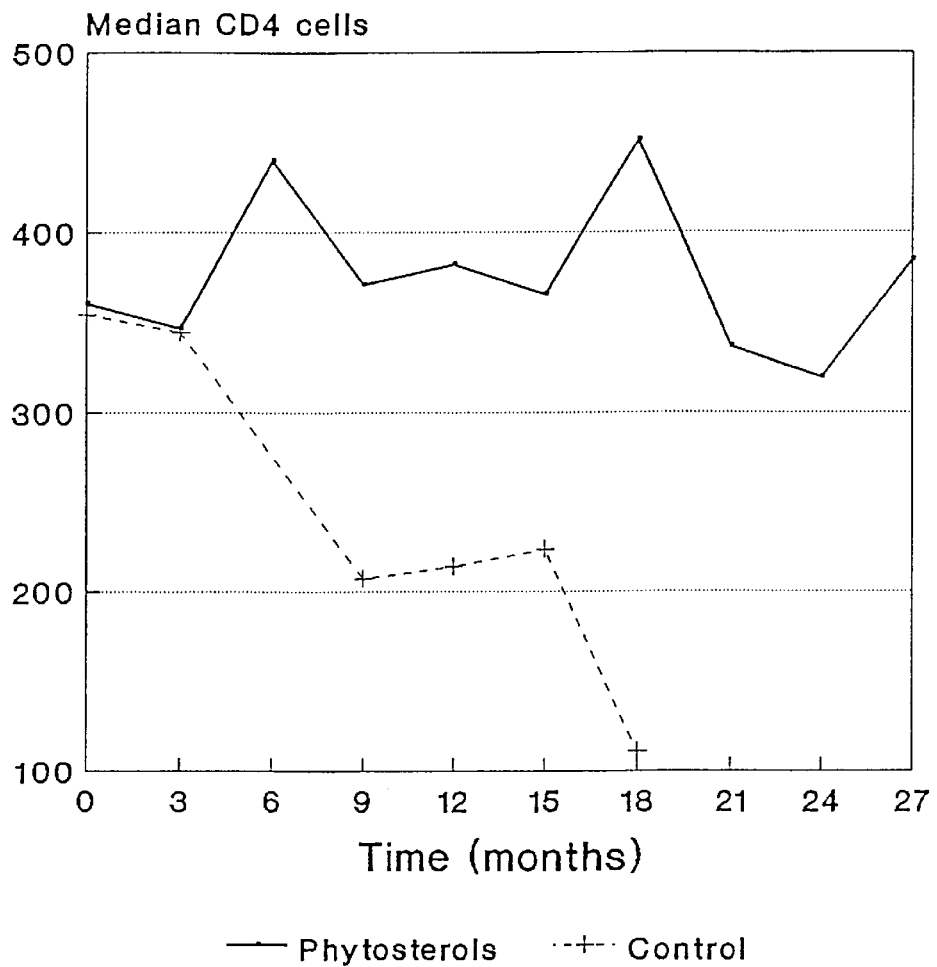
FIG. 3 shows the long term stability of the CD4 cell counts.
Figure 4:
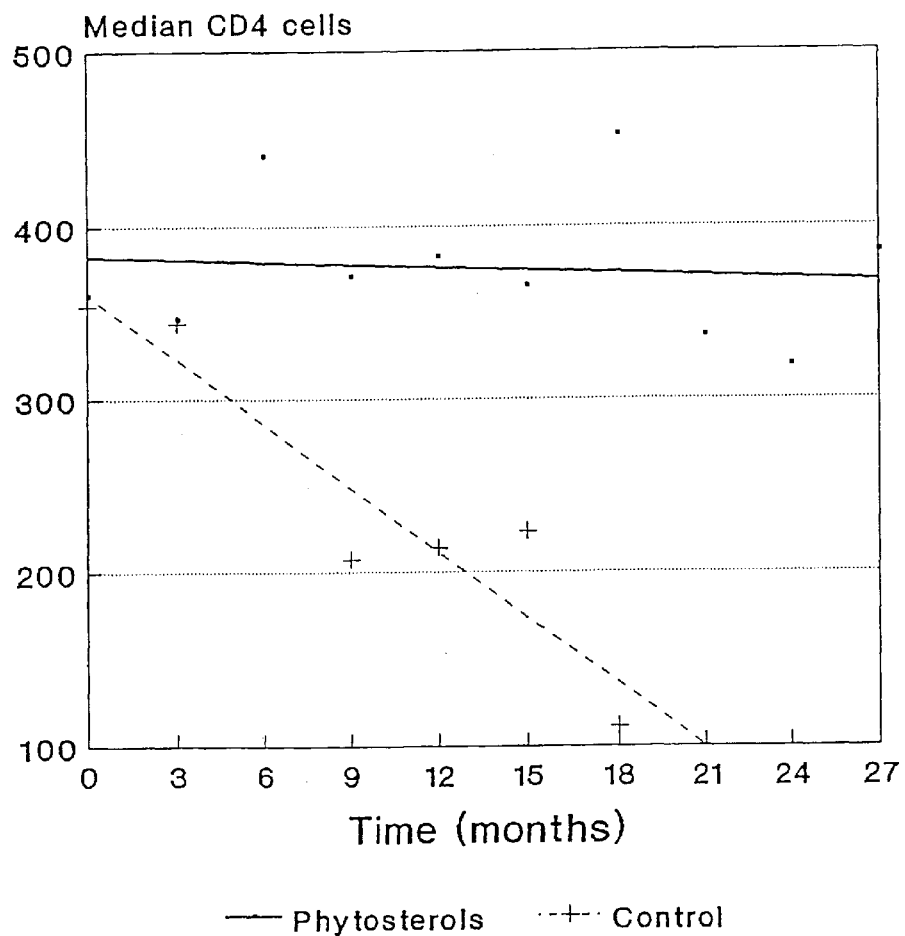
FIG. 4 shows regression analysis of a group of patients maintaining their CD4 cell numbers over an extended period of time.

Analysis of the long term data (>12 months tip to 27 months) in a similar fashion reveals the stability of the CD4 cell counts of this group of patients (FIG. 3). In parallel, the control patients data stops abruptly at 18 months since al these patients dropped out of the study (either died due to disease progression or decided to become treated subjects). Once again, regression analysis of the data indicates a straight line with a slope value of −2.44 (p=Not significant when compared to the baseline value) indicating that the group of patients maintain their CD4 cell numbers over an extended period of time (FIG. 4). At this point, it is important to recall that the BSS:BSSG mixture has been shown to have potent immunomodulatory properties and that they do not have direct anti-viral activities.

Figure 5:
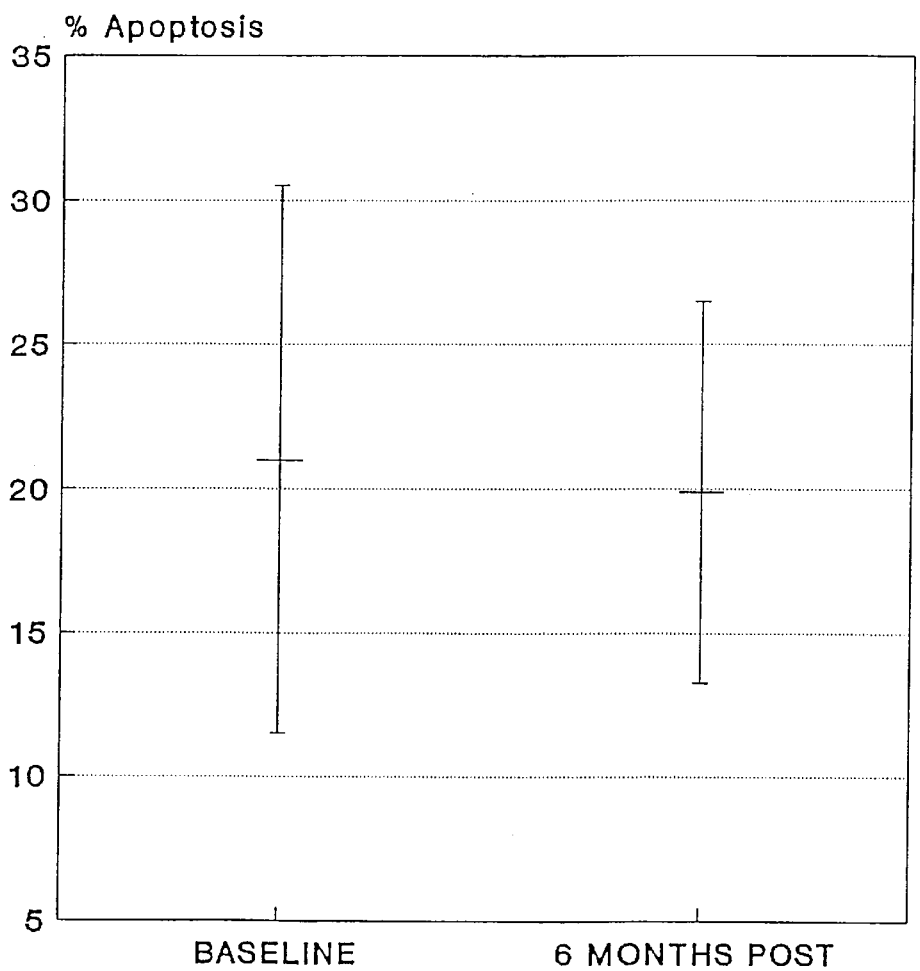
FIG. 5 shows the measurement of apoptosis in the lymphocyte population of the patients of FIG. 4.

The measurement of apoptosis in the lymphocyte population of these patients was conducted and the results are shown in FIG. 5. As can be seen, over a 6 months period, the degree of apoptosis (which accounts for a considerable loss of HIV infected cells as well as uninfected cells) decreased slightly although this was not statistically significant. This is an important finding since it is known that disease progression in HIV positive patients is accompanied by increases in the CD4 cell loss due to increased apoptosis. In our study population, over a period of 6 months, this marker has shown a slight decline although not statistically significant. This would seem to show that the BSS:BSSG capsules are capable of inhibiting the process of apoptosis.

Figure 6:
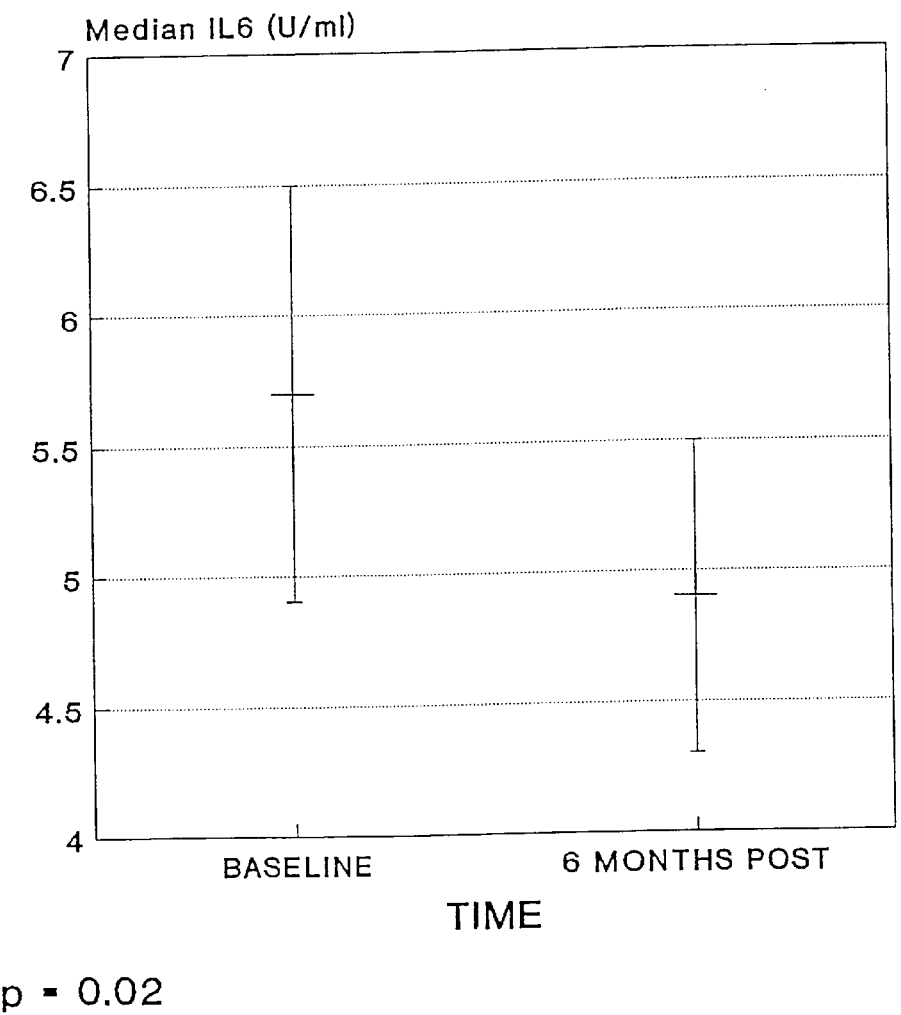
FIG. 6 shows the efficacy of the BSS:BSSG mixture in the HIV positive population.

Further evidence for the efficacy of the BSS:BSSG mixture in our population of HIV positive patients is shown in FIG. 6 which indicates that the serum levels of the pro-inflammatory factor IL6 decreased over a period of 6 months in the group of patients. This decrease is statistically significant (p=0.02). These results would indicate that active viral replication can be halted and that this would translate into stable CD4 cell numbers (as shown above) since as mentioned earlier, IL6 is a monokine (factor secreted by monocytes) which is implicated in the activation of latently infected cells of the host and the induction of active viral replication. Furthermore, in vitro data (not shown) has shown that the BSS:BSSG mixture is able to actively inhibit the synthesis and release of IL6 and TNFα by LPS activated monocytes prepared from the blood of healthy individuals.

Figure 7:
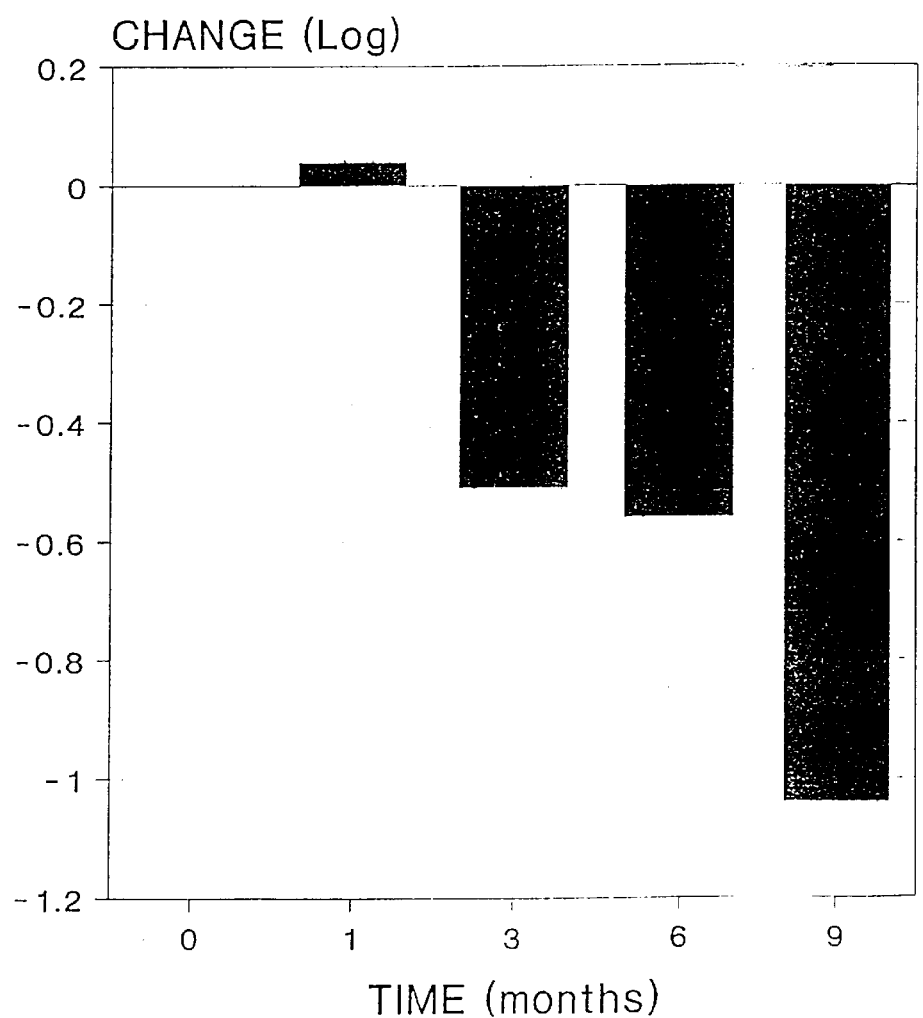
FIG. 7 shows the change in plasma viral loads of patients ingesting the BSS:BSSG mixture.

The data of plasma viral loads in this group of 80 patients ingesting the BSS:BSSG mixture shows that this marker declines steadily over a period of 9 months to reach a mean change of −1.04 log at 9 months. This is a steady but definite decline as follows: −0.51 at 3 months; −0.56 at 6 months and finally −1.04 at 9 months (FIG. 7). This decline is slow should one compare the decline induced by the use of anti-retroviral drugs. However, it should be remembered that the BSS:BSSG mixture does not have direct anti-viral activity but rather modulates the immune response so that the enhanced activities of the immune cells control viral replication indirectly.

Further Evidence of Efficacy of BSS:BSSG Mixture in Retroviral Infections

As previously reported, the cat equivalent of the HIV is a virus which infects cells bearing the CD4 molecule and this virus induces immune suppression in a similar fashion to the human counterpart. Cats infected with the FIV is thus an ideal model to study the biological effects of drugs on disease progression and to determine efficacy of the drug in question.

Figure 8:
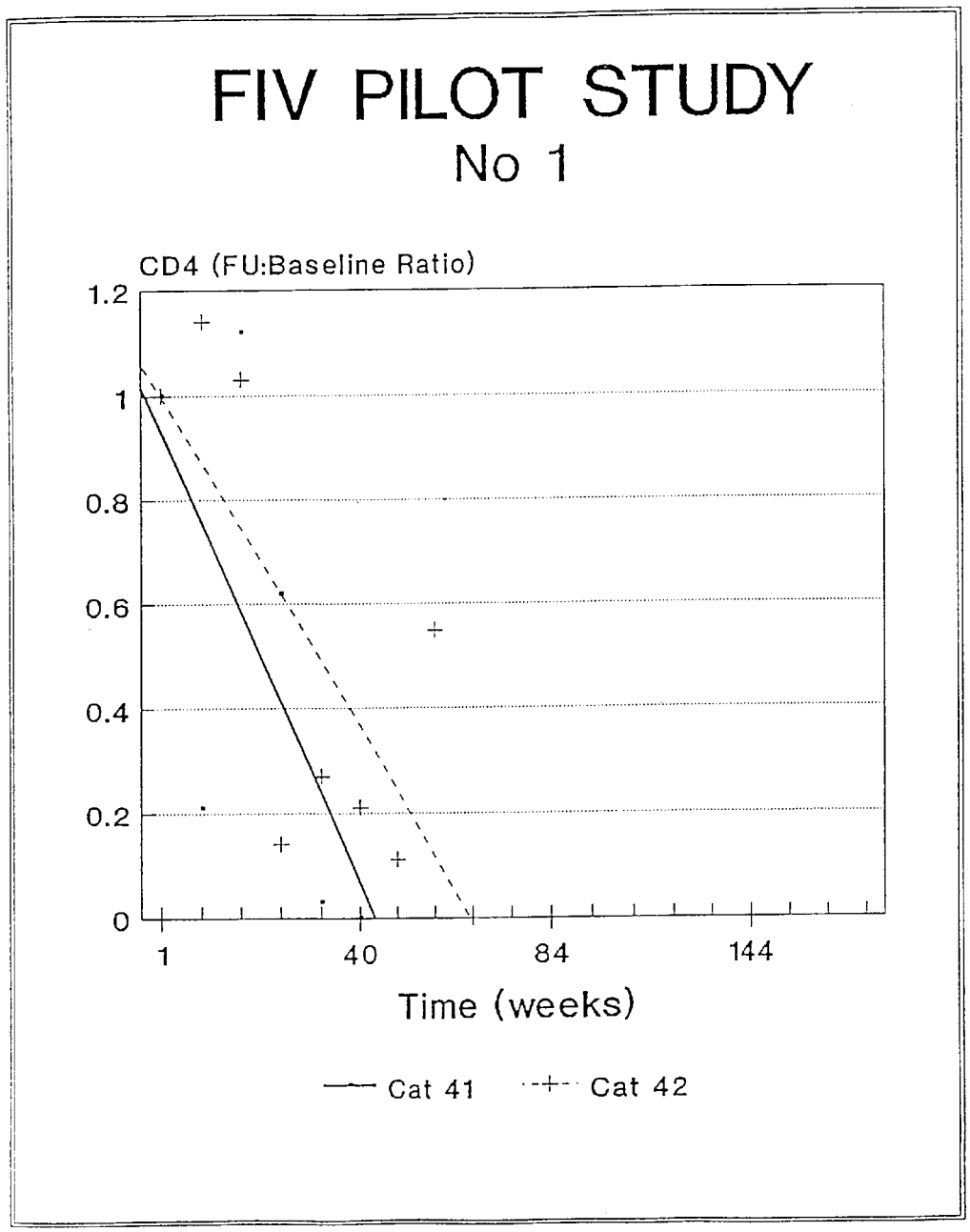
FIGS. 8 and 9 show the results of FIV pilot study 1.
Figure 9:
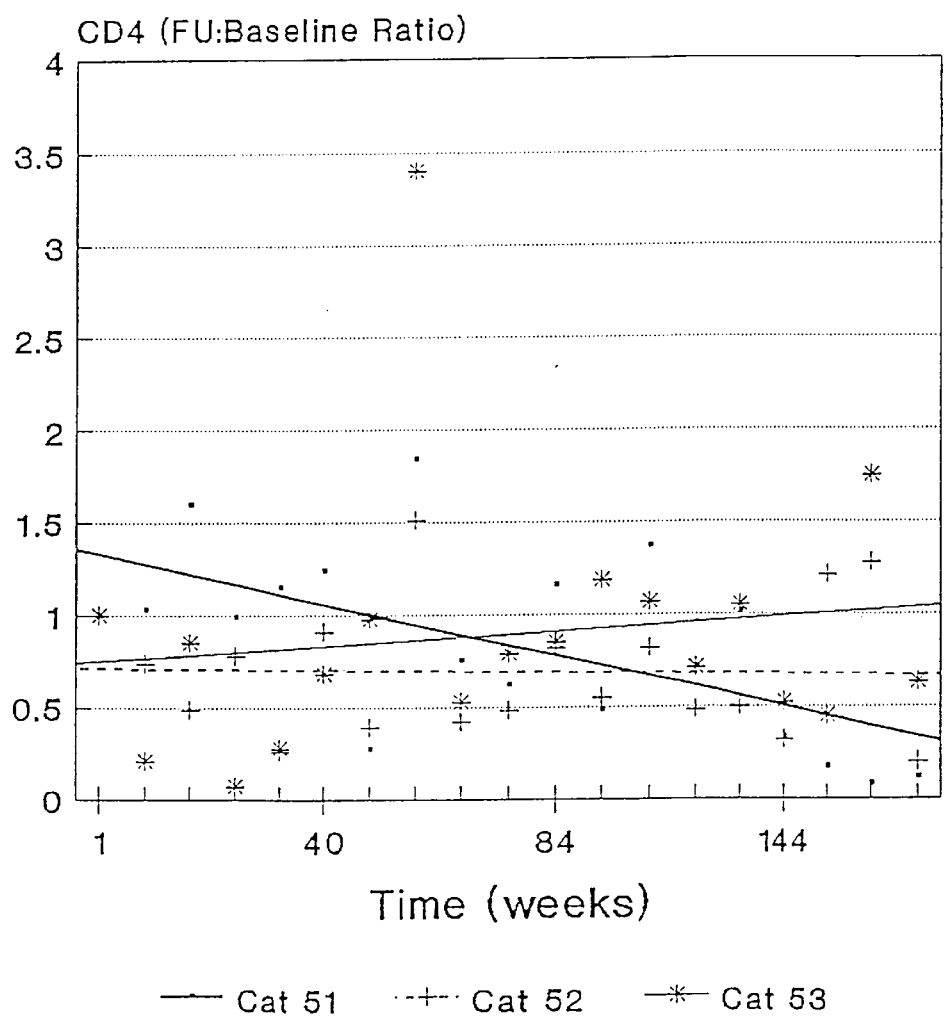

FIV Pilot study No 1:

As can be seen, 2 cats which were not treated decreased their CD4 cell numbers rapidly over a period of 60 weeks and finally succumb to disease (FIG. 8). In comparison, the 3 cats which received the BSS:BSSG mixture maintained their counts and are still alive with no signs of disease progression (FIG. 9). Only 1 cat (cat 51) has shown a decline in its CD4 cell number over this study period but clinically no overt signs of disease.

FIV Pilot study No 2:

Due to the fact we had no knowledge of time of infection in these cats described above, it was decided to repeat the above experiment using a well defined strain of the FIV (Petuluma strain; acknowledgment to Prof. N C Pedersen) and to experimentally infect a group of cats. For this, 33 cats were infected using the same aliquot of infected blood and the parameters mentioned above were monitored. Two new groups of cats were formed: group 1 consisted of 16 cats which received the BSS:BSSG capsules whereas group 2 cats (n=17) received placebo capsules. They were housed in identical facilities at the university and were fed standard diet of commercial cat food and ad lib tap water and dry cat food.

Figure 10:
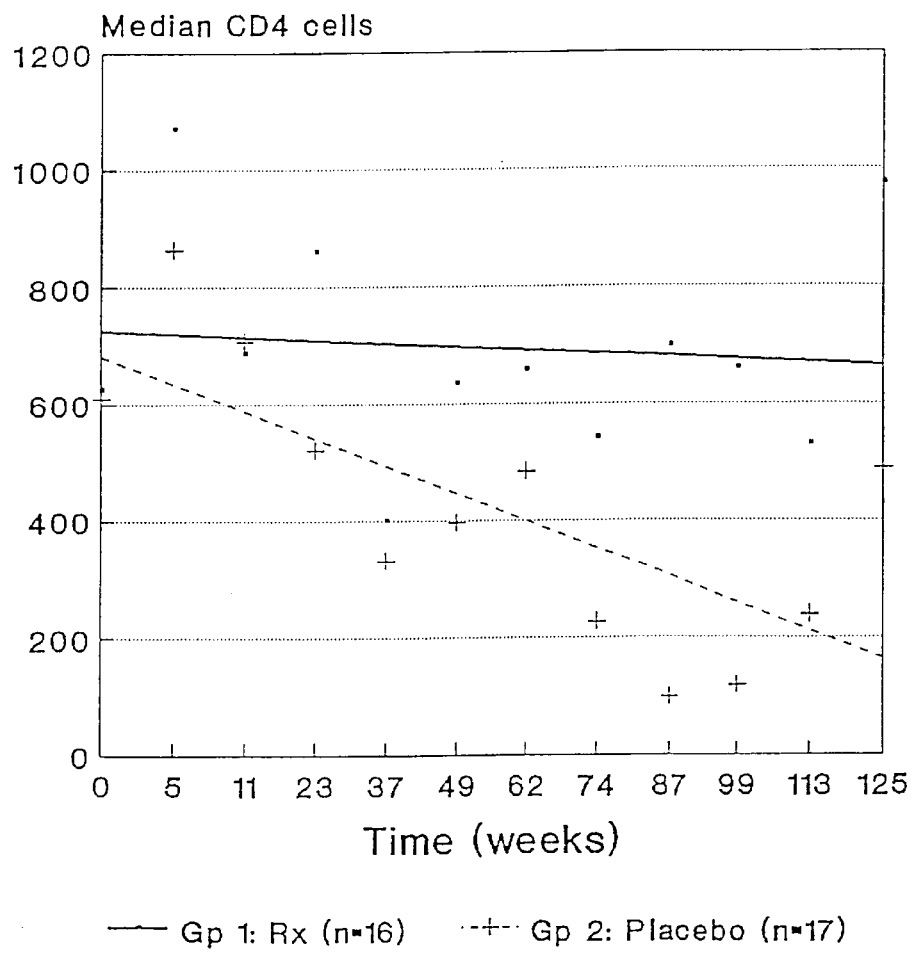
FIG. 10 shows the results of FIV pilot study 2.

As shown in FIG. 10, when the regression line of the median CD4 cell numbers for the two groups are compared, it is evident that those cats on the placebo capsules are showing a decline in their cell numbers over a period of 125 weeks whereas the cats receiving the active BSS:BSSG capsules are maintaining their CD4 cells, confirming the stability of these cells in the cats studied in pilot study number 1 as described above.

Of note is the following result of FIV transmission between infected queens and their offspring since recent literature reported that the FIV could be transmitted trans-placentally and post-natally in a similar fashion to the human virus. For this, infected queens were allowed to mate with uninfected male cats (litter brothers) and the outcome of the litters were monitored. As shown in Table I, there were equivalent number of litters on both side of this study but the rate of transmission and mortality in the kittens arising from the untreated queens differs significantly (p=0.001) from that observed in the treated queens.

TABLE I

| FIV transmission in BSS:BSSG-treated and untreated FIV positive queens: | | |
|---|---|---|
| | TREATED | UNTREATED |
| No of queens impregnated | 5 | 8 (3 litters resorbed) |
| No of kittens born | 19 | 22 |
| No of kittens surviving (FIV−) | 14 | 4 |
| Rate of transmission | 26% | 82% |
| Condition of kittens surviving | Good | Fair |

According to scientific literature [11], the normal rate of FIV transmission in experimentally infected cats is 78% which is confirmed in our small study. However, it must be noted that this rate is decreased to 26% in queens which received the phytosterols, implying that these immuno-modulatory plant compounds could have important clinical use in HIV infected pregnant women.

REFERENCES

1. Schnittman S M, Lane H C, et al (1990): Preferential infection of CD4+memory T cells by human immunodeficiency virus type 1: evidence for a role in the selective T-cell functional defects observed in infected individuals. Proc. Natl. Acad. Sci. 87, 6058–6062.
2. Reuben J M and Larocco M (1988): Cellular immune responses in acquired immunodeficiency syndrome. Clin. Lab. Sci. 1, 90–95.
3. Clerici M, Hakim F T, et al (1993): Changes in Interleukin-2 and Interleukin-4 production in asymptomatic, human immunodeficiency virus-seropositive individuals. J. Clin. Invest. 91, 759–765.
4. Kritzinger J J (1993): Rheumatological manifestations of the human immunodeficiency virus. Spes. Med. November 1993, 50–54.
5. Zinkernagel R M and Hengartner H (1994): T-cell-mediated immunopathology versus direct cytolysis by virus: implications for HIV and AIDS. Immunol, Today 15, 262–268.
6. Mendelow B V and Davidoff A N (1994): T-cell death in AIDS: murder or suicide? Spes. Med. February 1994, 43–46.
7. Breen E C, Rezai A R, et al (1990): Infection with HIV is associated with elevated IL6 levels and production. J. Immunol, 144, 480–484.
8. Herbein G, Keshav S. et al (1994): HIV-1 induces tumour necrosis factor and IL1 gene expression in primary human macrophages independent of productive infection. Clin. Exp. Immunol. 95, 442–449.
9. Pedersen N C, Ho E, et al (1987): Isolation of a T lymphotrophic virus from domestic cats with an immunodeficiency-like syndrome. Science 235, 790–793.
10. Bouic P J D, Etsebeth S. et al (1996): Beta-Sitosterol and Beta-Sitosterol glucoside stimulate human peripheral blood lymphocyte proliferation: implications for their use as an immunomodulatory vitamin combination. Int. J. Immunopharmac. 18, 693–700.
11. O'Neil L L, Burkhard M J, et al (1996): Frequent peri-natal transmission of the FIV by clinically infected cats. Virol. 70, 2894–2901.

I claim:

1. A method of stabilizing CD4 cell numbers in an HIV infected individual by administering a mixture of BSS and BSSG to the individual in a ratio of BSS:BSSG between 1:1 to 500:1.

2. The method according to claim 1 in which the mixture is administered in capsule form.

3. The method according to claim 1 in which the ratio of BSS:BSSG is of the order of 100:1.

4. A method of decreasing the plasma viral load and degree of apoptosis of lymphocytes in the peripheral blood of HIV positive individuals including the step of administering to that individual a mixture of BSS and BSSG in a BSS:BSSG ratio of between 1:1 and 500:1 in capsule form.

5. A method of decreasing the serum levels of IL6 in the peripheral bloods of HIV positive individuals including the step of administering to that individual a mixture of BSS and BSSG in a BSS:BSSG ratio of between 1:1 and 500:1 in capsule form.

* * * * *